United States Patent [19]
Klimt

[11] Patent Number: 4,627,430
[45] Date of Patent: Dec. 9, 1986

[54] INHALATOR APPARATUS

[76] Inventor: Hans U. Klimt, Rufenbergweg 14, D-7912 Weissenhorn-Bubenahusen, Fed. Rep. of Germany

[21] Appl. No.: 725,426

[22] Filed: Apr. 22, 1985

[30] Foreign Application Priority Data

May 23, 1984 [DE]  Fed. Rep. of Germany ....... 3419148

[51] Int. Cl.[4] ........................................... A61M 11/00
[52] U.S. Cl. ................................ 128/200.17; 239/338
[58] Field of Search ................... 128/200.17; 239/338, 239/380, 7, 223, 224

[56] References Cited

U.S. PATENT DOCUMENTS

| | | | |
|---|---|---|---|
| 2,783,088 | 2/1957 | Butler | 239/380 |
| 3,229,450 | 1/1966 | Stern | 128/200.17 |
| 3,812,853 | 5/1974 | Crain | 128/200.17 |
| 4,026,285 | 5/1977 | Jackson | 128/200.17 |
| 4,301,970 | 11/1981 | Craighero | 128/200.17 |

FOREIGN PATENT DOCUMENTS

| | | |
|---|---|---|
| 410681 | 3/1925 | Fed. Rep. of Germany ...... 239/380 |
| 3242128 | 6/1983 | Fed. Rep. of Germany . |
| 8328261 | 9/1983 | Fed. Rep. of Germany . |

*Primary Examiner*—Henry J. Recla
*Attorney, Agent, or Firm*—Thomas W. Speckman

[57] ABSTRACT

In an inhalator apparatus including a container for liquid inhalant, the tip of a suction cone adapted to be rotated by an electric motor is submerged in liquid inhalant and a zone of spray is produced along the upper peripheral edge of the suction cone. The mixture of vaporized liquid inhalant and air is discharged in the form of a fine mist from an aerosol outlet. Improvements obtained in the degree of vaporization and mixing according to the present invention are achieved by utilizing a lightweight suction cone of simple construction, with vanes of a radial blower extending upwardly from the peripheral edge of the suction cone. The radial blower is affixed to the suction cone and is rotatable. The air intake terminates in or above the space defined by the vanes of the radial blower.

20 Claims, 2 Drawing Figures

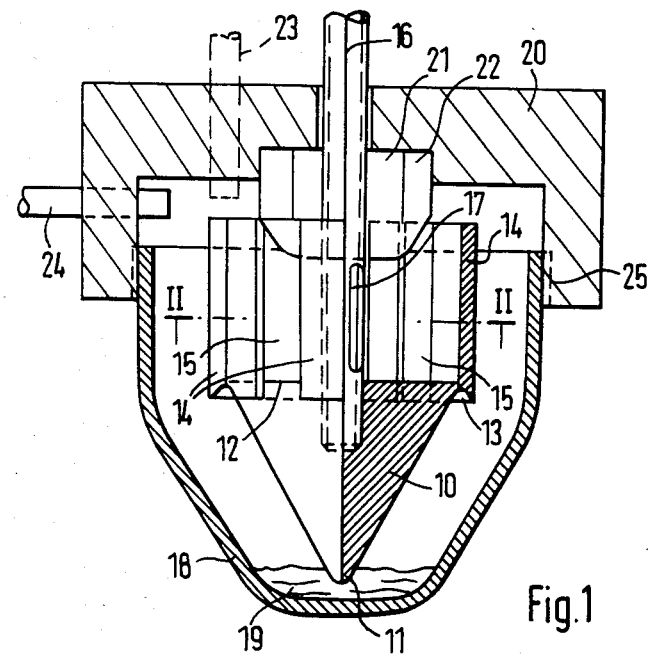
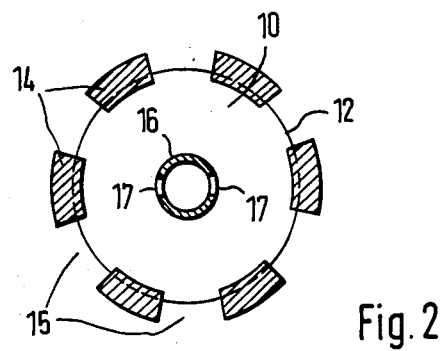

INHALATOR APPARATUS

BACKGROUND OF THE INVENTION

1. Field of the Invention

The present invention relates to an inhalator apparatus including a container for holding a liquid inhalant, in which the tip of a suction cone adapted to be rotated by an electric motor is submerged in liquid inhalant and rotated to produce a zone of spray along the upper peripheral edge of the suction cone, an air inlet terminates in the spray zone, and the mixture of liquid inhalant and air is discharged in the form of a fine mist from an aerosol outlet.

2. Description of the Prior Art

An inhalator apparatus of this general type is described in German Patent Publication No. OS 32 42 128. In this prior art inhalator, the suction cone, by virtue of its rotary motion, causes the liquid inhalant to be swirled up on its exterior surface until it reaches the peripheral rim of the cone. There the inhalant is dispersed by centrifugal force and is vaporized, creating a zone of fine mist or spray. The air inlet comprises several intake pipes which run parallel to the drive shaft of the suction cone and are grouped around the suction cone such that their openings are located below the peripheral edge of the suction cone and thus below the spray zone. The aerosol outlet is located above the spray zone, causing the intake air on its way to the outlet opening to pass through the spray zone where it is mixed with the vaporized inhalant.

In this prior art inhalator, uniform mixing of the intake air with the vaporized inhalant is difficult to achieve because of the asymmetrical placement of suction cone and air intake. Moreover, vaporization of the liquid inhalant is not fine enough and depends in large measure on the suction action at the aerosol outlet.

Improvement in the degree of vaporization of liquid inhalant is achieved with an inhalator disclosed in German Utility Model No. 83 28 261. In this inhalator, a hollow suction cone is enhanced in terms of its surface area by a hollow cylindrical vortical structural member joined to the peripheral edge of the suction cone, the two component parts in communication by means of a chamber disposed in front and provided with radial bores. The side of the vortical part facing away from the suction cone has a depression in the center from which additional radial bores spread outwardly. The tubular air intake is concentric with the drive shaft of the suction cone and is inserted into the depression provided in the vortical part. The aerosol discharge opening is located above the vortical member.

In this prior art inhalator, liquid inhalant is caused to swirl up on the exterior and interior walls of the hollow suction cone and is vaporized along the peripheral edge and/or in the radial bores of the vortical part. While this results in an increase in the volume of liquid inhalant conveyed, the degree of vaporization is not improved. The extent of mixing of vaporized inhalant with intake air is improved somewhat due to locating the air intake in the center. However, to achieve this result, a voluminous and complex suction cone is required and this is a serious drawback in view of the necessary high rotational speed.

SUMMARY OF THE INVENTION

It is an object of the present invention to provide an inhalator apparatus which employs a lightweight suction cone of simple construction to obtain substantial improvements in the degree of vaporization and the extent of mixing of vaporized inhalant with intake air.

This is accomplished according to the present invention in that vanes of a radial blower extend upwardly from the peripheral edge of the suction cone. The radial blower may be connected to the suction cone and is rotatable. The air intake terminates in or above the space enclosed by the vanes of the radial blower.

This construction of the suction cone provides that at the peripheral edge of the suction cone, where vaporization of the liquid inhalant takes place, a stream of air is produced by the radial blower which is symmetrically dispersed under pressure upon the vaporized inhalant to be mixed with it. This mixing action is independent of the suction effect at the aerosol outlet. An excellent degree of mixing of intake air with conveyed and vaporized liquid inhalant is achieved, and the extent of vaporization is improved due to the pressurized air which favors vaporization, that is, the formation of minute droplets of inhalant, along the peripheral edge of the suction cone. The suction cone may be of small size and simple construction.

The radial blower, according to one embodiment, comprises vanes formed by solid wall sections of a hollow cylindrical member between longitudinal slots in the cylindrical wall. The hollow cylinder is integrally joined to the peripheral edge of the suction cone and vanes project radially from the peripheral edge of the suction cone toward the container wall. The longitudinal slots extend to the peripheral edge of the suction cone. This transition from the suction cone to vanes of the radial blower provides improved vaporizing action because compressed air directed by the radial blower converges with the flow of liquid inhalant along the peripheral edge of the suction cone. Moreover, the inner sides of the vanes are displaced slightly inwardly from the peripheral edge toward the center of the suction cone. This reduces the amount of material required for construction of the radial blower.

The degree of vaporization and mixing are further improved, according to another embodiment, in that the undersides of the vanes facing the peripheral edge of the suction cone extend beyond the peripheral edge of the suction cone toward the tip of the cone, the distance from the cone surface steadily increasing toward the tip of the cone.

According to another embodiment, the suction cone and the vanes are made of a plastic material by injection molding and the single combination part is fixedly attached to the drive shaft of an electric motor. In this manner, the suction cone is still cost effective to manufacture as a unitary member.

Symmetrical dispersal of the air distributed by the radial blower is achieved, according to another embodiment, in that the drive shaft is connected to the suction cone concentrically with the peripheral edge of the cone. The drive shaft is hollow and is provided with apertures for passage of air into the region between the vanes of the radial blower and the apertures of the drive shaft.

According to another embodiment, intake air is conveyed to the radial blower by an air inlet which comprises a pipe section disposed in the portion of the housing which limits the space above vanes of the radial blower. This provides sufficient air flow because the radial blower itself exerts a strong suction action. In this embodiment, mounting the drive shaft of the suction cone poses no problem whatsoever.

According to another embodiment, the aerosol outlet is located near the upper sides of the radial blower vanes and projects radially outwardly to discharge the aerosol from above the vaporization and mixing zones.

The volume of liquid inhalant conveyed may be increased according to yet another embodiment, in that the suction cone comprises a hollow body with an opening at the tip.

To obtain quiet operation of the high speed suction cone, another embodiment provides that the blower vanes are uniformly spaced around the peripheral edge of the suction cone. Construction of the suction cone with vanes of the radial blower thereon is simplified, according to one embodiment, in that vanes are formed by wall sections between longitudinal slots in a hollow cylindrical body, the longitudinal slots extending through the entire thickness of the hollow cylindrical body and extending for the length of the vanes.

Another advantageous embodiment is characterized by both the vanes and the longitudinal spaces therebetween having approximately the same width.

BRIEF DESCRIPTION OF THE DRAWING

The invention will be described in further detail with reference to an embodiment illustrated in the drawing, in which:

FIG. 1 is a sectional view of the portion of the inhalator apparatus which includes the suction cone and the radial blower;

FIG. 2 is a cross-sectional view taken along the line II—II of FIG. 1, showing the vanes affixed to the suction cone.

DESCRIPTION OF PREFERRED EMBODIMENTS

Liquid inhalant 19 is supplied to container 18, which is preferably made of a transparent material and is attached in a conventional manner to housing 20, as indicated by connecting means 25 in the form of a bayonet or screw connection. Rotatably mounted in housing portion 20 is drive shaft 16 of an electric motor, as shown by bearing parts 21 and 22. The lower end of hollow drive shaft 16 is fixedly attached to solid suction cone 10 to impart rotational movement to it. Peripheral edge 12 of suction cone 10 merges with the radial blower comprising vanes 14. Vanes 14 are integrally formed with the peripheral edge 12 of suction cone 10, with the inner walls of vanes 14 displaced slightly inwardly from peripheral edge 12 toward the center of suction cone 10. Vanes 14 are separated from each other by longitudinal slots 15. As shown in the sectional view of FIG. 2, vanes 14 form part of a hollow cylinder, the wall of which is uniformly divided by longitudinal slots 15, with vanes 14 being solid wall sections between slots 15. Longitudinal slots 15 are of uniform measurement relative to the longitudinal dimension and thickness of vanes 14, permitting suction cone 10 with vanes 14 thereon to be manufactured in one piece. Slots 15 extend to peripheral edge 12 of suction cone 10 so that the air taken in and conveyed radially outwardly by the radial blower is mixed with vaporized inhalant directly in the region of peripheral edge 12, where the vaporization of liquid inhalant conveyed upwardly on the surface of suction cone 10 takes place.

If drive shaft 16 is hollow and is provided with apertures 17 leading to the volume enclosed by vanes 14, the air taken in is symmetrically dispersed by the radial blower upon the mist of vaporized inhalant.

Since the radial blower provides sufficient suction, it is possible to have the air inlet terminate above the space enclosed by vanes 14 of the radial blower, as indicated by air intake pipe section 23 mounted in housing portion 20. This simplifies mounting of the rotary drive shaft 16 since the intake air is no longer conveyed through drive shaft 16.

The undersides 13 of vanes 14 project beyond peripheral edge 12 toward tip 11 of suction cone 10, the distance from the cone surface continuously increasing toward tip 11. This feature improves the effectiveness of the vaporization zone.

Aerosol outlet 24 in the form of a pipe section mounted in housing portion 20 projects radially outwardly from suction cone 10 and is displaced slightly from the upper sides of vanes 14 so as to be located above the spray zone.

Suction cone 10 may also be constructed as a hollow body with an opening at tip 11. In this way, an additional stream of liquid inhalant may be conveyed up on the interior surface of suction cone 10. This flow of liquid inhalant also terminates near peripheral edge 12 where it is vaporized. The interior surface of hollow suction cone 10 is provided with struts or ribs and a bushing for fixedly mounting drive shaft 16.

I claim:

1. In an inhalator apparatus comprising a container for holding a liquid inhalant, a suction cone having an upper peripheral edge and a lower tip and mounted within said container such that said tip would be submerged in said liquid inhalant, means connected to said suction cone and extending through said container for rotating said suction cone about its axis rotated by an electric motor, an air inlet into said container, and an aerosol outlet from said container for discharging a mixture of liquid inhalant and air in the form of a fine mist, the improvement comprising a radial blower having a plurality of vanes (14) extending upwardly and radially from said peripheral edge (12) of said suction cone (10), said vanes (14) defining a hollow cylinder comprising longitudinal sections divided by longitudinal slots (15) of the hollow cylinder, said longitudinal sections being integral with said peripheral edge (12) and said longitudinal slpts (15) extending to said peripheral edge (12), said vanes (14) having inner surface sides displaced inwardly from said peripheral edge (12) toward the axis of said suction cone (10), and said vanes (14) having undersides (13) adjacent said peripheral edge (12) projecting below said peripheral edge (12) toward said tip (11) of said suction cone (10) and defining divergent surfaces in continuously increasing distance from the outer surface of said suction cone (10), said radial blower attached to said suction cone (10) and adapted to be rotated therewith, and said air intake communicating with the sapce enclosed by said vanes (14) of said radial blower.

2. Inhalator apparatus according to claim 1, characterized in that said suction cone (10) and said vanes (14) are integral and are made of a plastic material by injection molding and said rotating means comprises a driveshaft fixedly attached to said cone and adapted to be rotated by an electric motor.

3. Inhalator apparatus according to claim 2, characterized in that said drive shaft (16) attached to said suction cone (10) is concentric with its said periphral edge (12), and said drive shaft (16) is a hollow tube provided with apertures (17) in the region of said vanes (14) to provide passage of air between said vanes (14) and said apertures (17).

4. Inhalator apparatus according to claim 2, characterized in that a housing portion (20) is mounted near the top of and extends above said container, and said air intake comprises a pipe section (23) mounted in said housing portion (20), and said air intake terminates in a space above said radial blower vanes (14).

5. Inhalator apparatus according to claim 4, characterized in that said aerosol outlet (24) extends radially outwardly from a region near the upper sides of said radial blower vanes (14).

6. Inhalator apparatus according to claim 4, characterized in that said vanes (14) are uniformly spaced along said peripheral edge (12) of said suction cone (10).

7. Inhalator apparatus according to claim 6 characterized in that said vanes (14) comprising longitudinal sections of said hollow cylinder are formed by subdividing said cylinder with longitudinal slots (15) of uniform measurement relative to the longitudinal dimension and thickness of said vanes (14).

8. Inhalator apparatus according to claim 7, characterized in that said vanes (14) and said longitudinal slots (15) are of approximately the same width.

9. Inhalator apparatus according to claim 1, characterized in that said suction cone (10) and aid vanes (14) are integral and are made of a plastic material by injection molding and said rotating means comprises a driveshaft fixedly attached to said cone and adapted to be rotated by an electric motor.

10. Inhalator apparatus according to claim 1, characterized in that a housing portion (20) is mounted near the top of and extends above said container, and said air intake comprises a pipe section (23) mounted in said housing portion (20), and said air intake terminates in a space above said radial blower vanes (14).

11. Inhalator apparatus according to claim 1, characterized in that said aerosol outlet (24) extends radially outwardly from a region near the upper sides of said radial blower vanes (14).

12. Inhalator apparatus according to claim 1, characterized in that said vanes (14) are uniformly spaced along said peripheral edge (12) of said suction cone (10).

13. Inhalator apparatus according to claim 1, characterized in that said vanes (14) comprising longitudinal sections of said hollow cylinder are formed by subdividing said cylinder with longitudinal slots (15) of uniform measurement relative to the longitudinal dimension and thickness of said vanes (14).

14. Inhalator apparatus according to claim 1, characterized in that said vanes (14) and said longitudinal slots (15) are of approximately the same width.

15. In an inhalator apparatus comprising a container for holding a liquid inhalant, a suction cone having an upper peripheral edge and a lower tip and mounting within said container such that said tip would be submerged in said liquid inhalant, means connected to said suction cone and extending through said container for rotating said suction cone about its axis by an electric motor, an air inlet into said container, and an aerosol outlet from said container for discharging a mixture of liquid inhalant and air in the form of a fine mist, the improvement comprising a radial blower having a plurality of vanes (14) extending upwardly and radially from said peripheral edge (12) of said suction cone (10), said vanes (14) having undersides (13) adjacent said peripheral edge (12) and profecting below said peripheral edge (12) toward said tip (11) and defining divergent surfaces continuously increasing in distance from the outer surface of said suction cone (10), said radial blower attached to said suction cone (10) and adapted to be rotated therewith, and said air intake communicating with the enclosed by said vanes (14) of said radial blower.

16. Inhalator apparatus according to claim 15, characterized in that said vanes (14) comprise longitudinal sections of a hollow cylinder divided by longitudinal slots (15), said hollow cylinder integral with said peripheral edge (12) of said suction cone (10), said vanes (14) projecting radially from said peripheral edge (12), and said longitudinal slots (15) extending to said peripheral edge (12) of said suction cone (10).

17. Inhalator apparatus according to claim 15, characterized in that inner sides of said vanes (14) are displaced inwardly from said peripheral edge (12) of said suction cone (10) toward the center of suction cone (10).

18. Inhalator apparatus according to claim 15, characterized in that a drive shaft (16) of said eletric motor is attached to said suction cone (10) whereby said drive shaft (16) is concentric with said peripheral edge (12), and said drive shaft (16) is a hollow tube provided with apertures (17) in the region of said vanes (14) to provide passage of air between said vanes (14) and said apertures (17).

19. Inhalator apparatus according to claim 15, characterized in that a housing portion (20) is mounted near the top of and extends above said container, and said air intake comprises a pipe section (23) mounted in said housing portion (20), and said air intake terminates in a space above said radial blower vanes (14).

20. In an inhalator apparatus comprising a container for holding a liquid inhalant, a suction cone having an upper peripheral edge with a lower tip and mounted within said container in such that said tip would be submerged in said liquid inhalant, means connected to said suction cone and extending through said container for rotating said suction cone about its axis by an electric motor, an air inlet into said container, and an aerosol outlet from said container for discharging a mixture of liquid inhalant and air in the form of a fine mist, the improvement comprising a radial blower having a plurality of vanes (14) extending upwardly and radially from said peripheral edge (12) of said suction cone (10), said radial blower attached to said suction cone (10) and adapted to be rotated therewith, said rotating means comprises a drive shaft (16) fixedly attached to said suction cone (10) are adapted to be rotated by an electric motor whereby said drive shaft (16) is concentric with said peripheral edge (12) and comprises a hollow tube provided with apertures (17) in the region of said vanes (14) to provide passage of air between said vanes (14) and said apertures (17).

* * * * *